United States Patent
Mistretta et al.

(10) Patent No.: US 12,042,649 B2
(45) Date of Patent: Jul. 23, 2024

(54) CORTICAL STIMULATION AND RECORDING ELECTRODE AND METHOD FOR MAKING SUCH ELECTRODE

(71) Applicant: Spes Medica Srl, Genoa (IT)

(72) Inventors: Matteo Mistretta, Genoa (IT); Giorgio Facco, Genoa (IT)

( * ) Notice: Subject to any disclaimer, the term of this patent is extended or adjusted under 35 U.S.C. 154(b) by 1070 days.

(21) Appl. No.: 16/473,530

(22) PCT Filed: Jan. 2, 2018

(86) PCT No.: PCT/IB2018/050014
§ 371 (c)(1),
(2) Date: Jun. 25, 2019

(87) PCT Pub. No.: WO2018/122824
PCT Pub. Date: Jul. 5, 2018

(65) Prior Publication Data
US 2020/0121919 A1 Apr. 23, 2020

(30) Foreign Application Priority Data
Jan. 2, 2017 (IT) .......................... UA2017A000007

(51) Int. Cl.
*A61N 1/05* (2006.01)
*A61B 5/00* (2006.01)
*A61B 5/293* (2021.01)
*C09D 11/52* (2014.01)

(52) U.S. Cl.
CPC ............ *A61N 1/0531* (2013.01); *A61B 5/293* (2021.01); *A61B 5/6868* (2013.01); *C09D 11/52* (2013.01)

(58) Field of Classification Search
CPC ........ A61N 1/05; A61N 1/0531; A61B 5/291; A61B 5/6868; C09D 11/52
See application file for complete search history.

(56) References Cited

U.S. PATENT DOCUMENTS

| | | | |
|---|---|---|---|
| 6,032,065 A * | 2/2000 | Brown | A61B 5/282 |
| | | | 600/383 |
| 2004/0018297 A1 | 1/2004 | Davidson | |
| 2004/0121528 A1 | 6/2004 | Krulevitch | |
| 2007/0088417 A1 | 4/2007 | Schouenborg | |
| 2009/0012593 A1 * | 1/2009 | Benabid | A61N 1/0529 |
| | | | 607/116 |
| 2011/0213438 A1 | 9/2011 | Lima | |
| 2011/0237921 A1 | 9/2011 | Askin, III | |
| 2011/0264166 A1 | 10/2011 | Benabid | |
| 2015/0099959 A1 | 4/2015 | Bonmassar | |
| 2015/0202351 A1 | 7/2015 | Kaplan | |
| 2016/0059004 A1 * | 3/2016 | Mercanzini | A61B 5/24 |
| | | | 156/215 |

(Continued)

*Primary Examiner* — Christopher A Flory
(74) *Attorney, Agent, or Firm* — Themis Law (57) ABSTRACT

A cortical stimulating and recording electrode includes a flexible support element for a conductive element, the flexible support element having a head end and a tail end. The conductive element has a head contact and a tail contact, arranged respectively at the head end and tail end of the flexible support element, such that the conductive element transmits signals from the head contact to the tail contact and vice versa. Moreover, the conductive element is configured as a conductive track formed of a layer of conductive ink deposited on the flexible support element.

11 Claims, 6 Drawing Sheets

(56) References Cited

U.S. PATENT DOCUMENTS

| | | | |
|---|---|---|---|
| 2017/0079543 A1* | 3/2017 | Sadeghian-Motahar | ..................... A61B 5/055 |
| 2017/0224990 A1* | 8/2017 | Goldwasser | ......... A61N 1/0476 |
| 2018/0126155 A1* | 5/2018 | McLaughlin | ........ A61N 1/0534 |
| 2020/0091495 A1* | 3/2020 | Ghezzi | ................ H01M 4/0404 |

* cited by examiner

CORTICAL STIMULATION AND RECORDING ELECTRODE AND METHOD FOR MAKING SUCH ELECTRODE

The present invention relates to a cortical stimulating and recording electrode comprising a flexible support element for at least one conductive element, which flexible support element has a head end and a tail end.

The conductive element has at least one head contact and at least one tail contact, arranged at the head end and at the tail end of the flexible support element respectively, such that the conductive element transmits signals from the head end to the tail end and vice versa.

The invention particularly relates to intracranial electrodes and to the use thereof, both for recording signals and for brain stimulation.

Particularly the electrode is inserted into the skull of a patient in contact with the cortical surface, such to detect the brain activity of the patient.

The head contact detects such activity and, through the conductive element, transmits it to the tail contact that generally is connected, directly or by the use of further devices, to a connector of a signal reading, processing and displaying device.

Prior art known electrodes therefore are composed of a support made of silicone or similar material, on which metal plates are fastened which are the head contacts.

A conductive element is welded to each metal plate, composed of a metal wire covered by an insulating sheath whose end is welded to the tail contact.

An example of such an electrode is described in documents U.S. Pat. No. 4,903,702 and WO 2013/148637, whose contents has to be considered as an integral part of the present patent application.

From the above it is clear how the process for making prior art known electrodes is complicated and difficult and it requires considerable manual working to assemble the several components.

Such aspect affects not only production costs and time, but also the risk of breaking one or more components.

Moreover the use of metal wires for conducting signals limits the flexibility of the support element: an excessive deformation of the electrode upon insertion into the skullcap may affect the integrity of wires or of connections of wires with head and tail contacts.

The effectiveness of prior art known electrodes therefore is limited and it necessarily requires large holes to be made in the skullcap of the patient to insert the electrodes.

Therefore there is the unsatisfied need in prior art known devices to provide a cortical stimulating and recording electrode overcoming the above mentioned drawbacks.

The present invention achieves the above objects by providing a cortical stimulating and recording electrode as described hereinbefore, wherein the conductive element is composed of a conductive track composed of a layer of conductive ink deposited on the flexible support element.

The use of conductive ink allows a flexible electrode to be provided: the flexibility of the support element is not limited, while maintaining the electric conductivity of the conductive element.

A preferred embodiment provides a plurality of conductive elements.

Each conductive element particularly is composed of a conductive track and between each conductive track an insulating track is interposed which is composed of a layer of insulating flexible material.

Such configuration provides an electrode having the same functions of prior art known electrodes, but being made as a single piece and therefore, as it will be described below, can be produced automatically without the need of assembling different components.

Moreover according to a variant embodiment, the head and tail contacts are each one composed of a plate composed of a first layer of conductive ink.

By such improvement merely metal parts are completely eliminated from the electrode of the present invention, therefore is exhibits a complete flexibility with no constructional limits related to the assembling of components or possible breaking of wires.

In order to improve the conductivity of the electrode of the present invention, it is possible to provide the head end to have a second layer of metal material.

The provision of a second layer of metal material, allows not only conductivity to be improved.

The choice of providing a second layer of metal material is not a mere constructional choice, but it has advantageous aspects related to the field of application of the electrode of the present invention.

As said above, it is essential for electrodes used in direct contact with the brain to have small dimensions such to make easier to insert them in the skull, while limiting dimensions of the holes to be perforated in the bones of the skull.

The need of limiting the dimensions of the electrode is in conflict with the need related to signal recording, that provides to increase to the highest extent the recording region of the electrode, that is the head contact, in order to obtain a better signal recording.

As it will be more clear from the disclosure of some embodiments, the particular configuration of the electrode of the present invention provides a layer of flexible material, a layer of conductive ink deposition and a layer of insulating material.

The layer of insulating material preferably covers the conductive ink except for the head and tail contacts.

In order to increase the recording region, a second layer of metal material is deposited in contact with each head contact, such to enlarge the size of the recording region.

A further advantage of the provision of the second layer of metal material is the possibility of changing also the shape of the recording region, which can be selected depending on operational needs and can be obtained by a process depositing the second layer of metal material.

Finally besides the possibility of changing the dimension and shape of the recording region it is possible to change also the type of metal material used, such to give to the electrode of the present invention a high adaptability to operational needs, for example by selecting the most appropriate metal should the electrode be used for stimulation, recording etc.

Advantageously the second layer of metal material consists in binding a plurality of particles of metal material by depositing said metal material on the head end.

Due to the use of the electrode of the present invention, i.e. the direct contact with the brain of the patient, the metal material preferably is composed of inert material, such as gold or the like.

The stimulation activity provides an interaction between metal ions of the head contact and the brain of the patient, for such reason the use of an inert material guarantees non-toxic ions to be deposited at cortical level.

Such guarantee is not assured by the use of a simple conductive ink, that provides to use metal powders whose ions can be deposited on the cortical surface of the patient.

In addition of the above advantages, the fact that the second layer is composed of particles being deposited allows flexibility properties to be maintained unchanged.

The plates formed after depositing metal particles are not rigid since the metal particles are not rigidly connected to one another: when bending the support element they move away from each other and then they return back in their starting condition once the electrode is placed such to be used, guaranteeing a proper conductivity of the electrode.

Due to the above advantages, the present invention relates also to a cortical stimulating and recording kit comprising an electrode and a tubular element such as a cannula or the like.

Particularly the electrode of the kit of the present invention can be made according to one or more of the characteristics described above.

It is clear how such kit can have important advantages as regards the operating perspective.

Due to flexibility properties of the electrode, in order to place it in contact with the patient brain, it will be enough to insert the cannula inside the patient skull, to bend the electrode and to fit it into the cannula, till reaching the region of interest of the patient brain.

In this case the positioning of the electrodes will not require, unlike prior art known electrodes, to form large holes in the patient skull.

It is clear how the minimally invasive method for inserting the electrode described above, is a possibility advantageously obtained due to the particular characteristics of the electrode and of the kit of the present invention.

However such method can be selected on the basis of operating needs, namely if it is not clinically required to make a large hole on the patient skull, for instance if it necessary to insert complex arrays of electrodes, that can even require to operate on "exposed skull".

Obviously the kit of the present invention has all the advantages and characteristics of the electrode of the present invention.

The present invention finally relates to a method for making a cortical stimulating and recording electrode.

The method particularly comprises the following steps:
a) depositing a conductive ink on a layer of flexible material such to form one or more conductive tracks,
b) depositing a layer of insulating material such to form one or more insulating tracks interposed between said conductive tracks.

It is clear how such process can be completely automatic: once obtaining a film of flexible material, it is possible, by means of prior art known devices, to print the conductive tracks and the insulating tracks on the flexible material.

The film of flexible material can be made according to methods known in prior art and can be composed of any biocompatible flexible material, such as for example polyurethane, silicone or the like.

Therefore all the procedures for assembling and connecting the several metal parts of prior art known electrodes are avoided, which necessarily require a manual operating support.

Moreover all methods commonly used in prior art known devices are avoided, which are particularly difficult to automatize, such as for example the removal of material to obtain seats within which conductive ink has to be deposited (so called etching).

The method of the present invention allows a more productive approach on large scale for the electrode of the present invention to be obtained, which is easy to be industrialized, since it provides to directly deposit the conductive ink on the layer of flexible material.

It is further clear how, by a simple user interface, it is possible to set the printing of tracks such to obtain several shapes of the electrodes on the sheet of flexible material.

The sheet then can be cut such to obtain the individual electrodes.

Based on the characteristics described up to now and those described below, it is clear that one of the most important advantages is the possibility of obtaining various shapes, with a number of head contacts, tail contacts and conductive tracks as one desires.

There are no constructional obstacles that oblige to be limited to a specific shape and, regardless of the selected shape, the electrode maintains its flexibility properties unchanged.

Some shapes that can be created by the method of the present invention will be shown below.

Advantageously the method of the present invention can provide a step c) relating to the deposition of a first layer of conductive ink, so as to form a head contact and a tail contact positioned at the ends of the conductive tracks.

Even such step can be automatized and provided in combination with step a), such that conductive tracks and head and tail contacts can be obtained by a single deposition of conductive ink.

According to an improvement of the method of the present invention there is provided a step d) relating to the deposition of a second layer of metal material at the head contact and/or tail contact.

As said above the second layer of metal material can consist in depositing a plurality of particles of inert material such as gold or the like.

According to a preferred variant embodiment, the step d) takes place through a galvanic coating.

These and other characteristics and advantages of the present invention will be more clear from the following description of some embodiments shown in annexed drawings wherein.

It has to be noted that figures annexed to the present patent application show some embodiments of the electrode and of the method of the present invention, to better understand the described advantages and characteristics.

Therefore such embodiments have to be considered merely for illustration purposes and not as a limitation to the inventive concept of the present invention described above.

Figure 1:
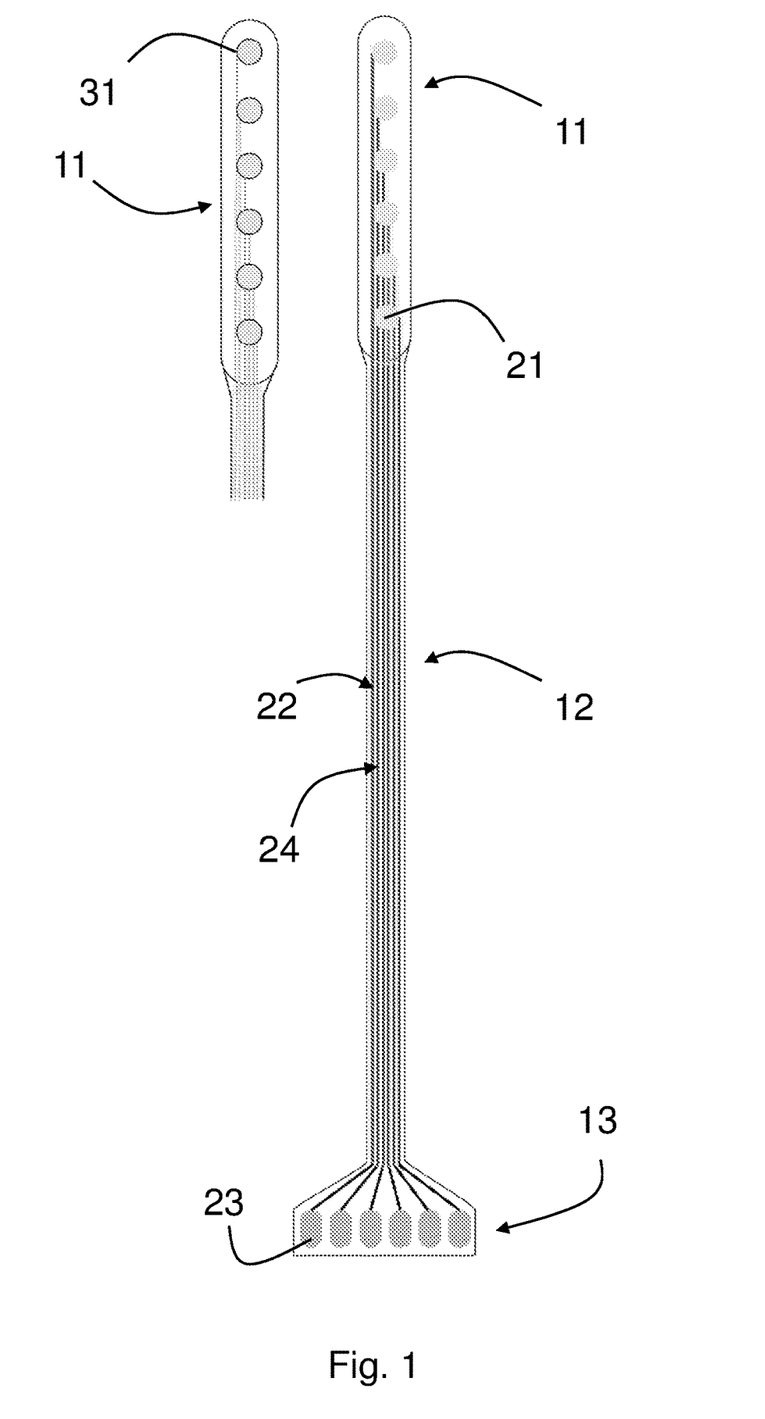
FIGS. 1 and 2a are two views of the cortical stimulating and recording electrode of the present invention according to a possible embodiment.
Figure 2A:
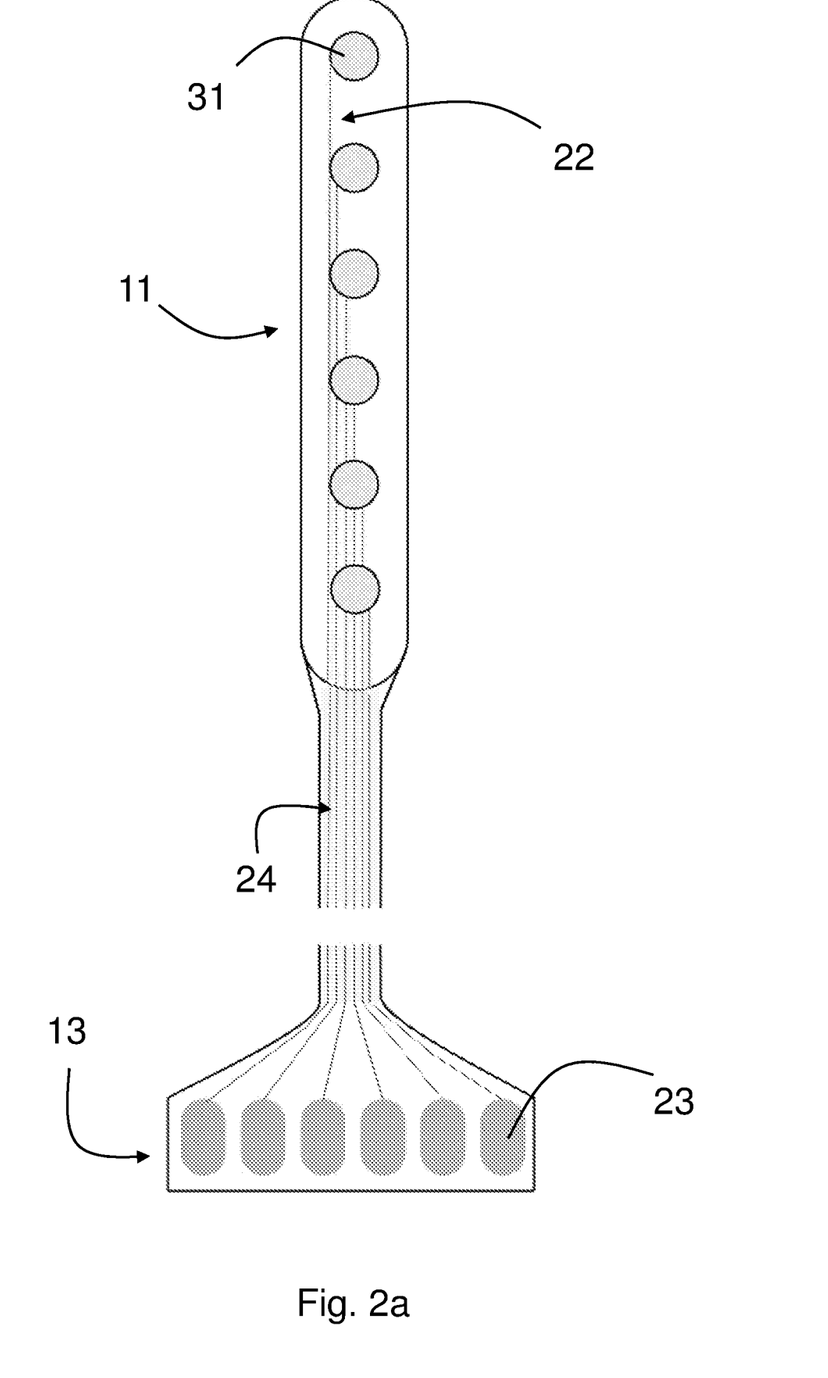

With particularly reference to FIGS. 1 and 2a, the cortical stimulating and recording electrode comprises a flexible support element having a head end 11, an intermediate part 12 and a tail end 13.

The support element is intended to support at least one conductive element 22 providing a head contact 21 and a tail contact 23, arranged at the head end 11 and tail end 13 respectively of the flexible support element.

In use, the head contact 21 is placed in contact with the cortical surface of the patient, such that the conductive element 22 can transmit signals from the head contact 21 to the tail contact 23.

According to the shown embodiment, the conductive element 22 is composed of a conductive track formed by a layer of conductive ink deposited on the flexible support element.

The flexible support element preferably is composed of a biocompatible plastic material such as polyurethane, silicone or the like.

Moreover with particular reference to figures, the electrode of the present invention provides a plurality of conductive elements 22 each one having a head contact 21 and a tail contact 23.

Moreover between each conductive element 22 an insulating material track 24 is interposed which is composed of a layer of flexible insulating material.

According to the shown embodiment, the head contact 21 and tail contact are each one composed of a plate composed of a layer of conductive ink.

As it will be clear below with reference to the description of the method of the present invention, the head contact 21, the conductive track 22 and the tail contact 23 can be obtained by a single deposition of conductive ink, such to form a single element for transmitting/receiving signals.

As in prior art known electrodes, the tail contacts 23 can be connected to devices intended to process or display information deriving from detected signals.

Particularly in FIG. 1, the head end 11 is shown in due different shapes.

In the variant on the right, the head end 11 has the head contact 21 composed of a first layer of conductive ink.

In the variant on the left, the head contact 21, in addition to the first layer of conductive ink comprises a second layer of metal material 31.

A specific embodiment of such layer of metal material 31 is described below with reference to FIG. 2b.

Preferably the second layer of metal material 31 is composed by binding a plurality of metal material particles obtained by depositing said metal material on the first layer of conductive ink.

The structure of the electrode of the present invention shown in FIGS. 1 and 2a therefore provides a flexible support element supporting six tail contacts 23 communicating with six corresponding head contacts 21 through six conductive tracks 22.

Each conductive track 22 is separated by an insulating material track 24.

Therefore the electrode is completely flexible and foldable without affecting the conductivity of the several components: thus it can be bent along its longitudinal axis such to be fitted into a cannula and then placed in contact with the patient brain.

Figure 2B:
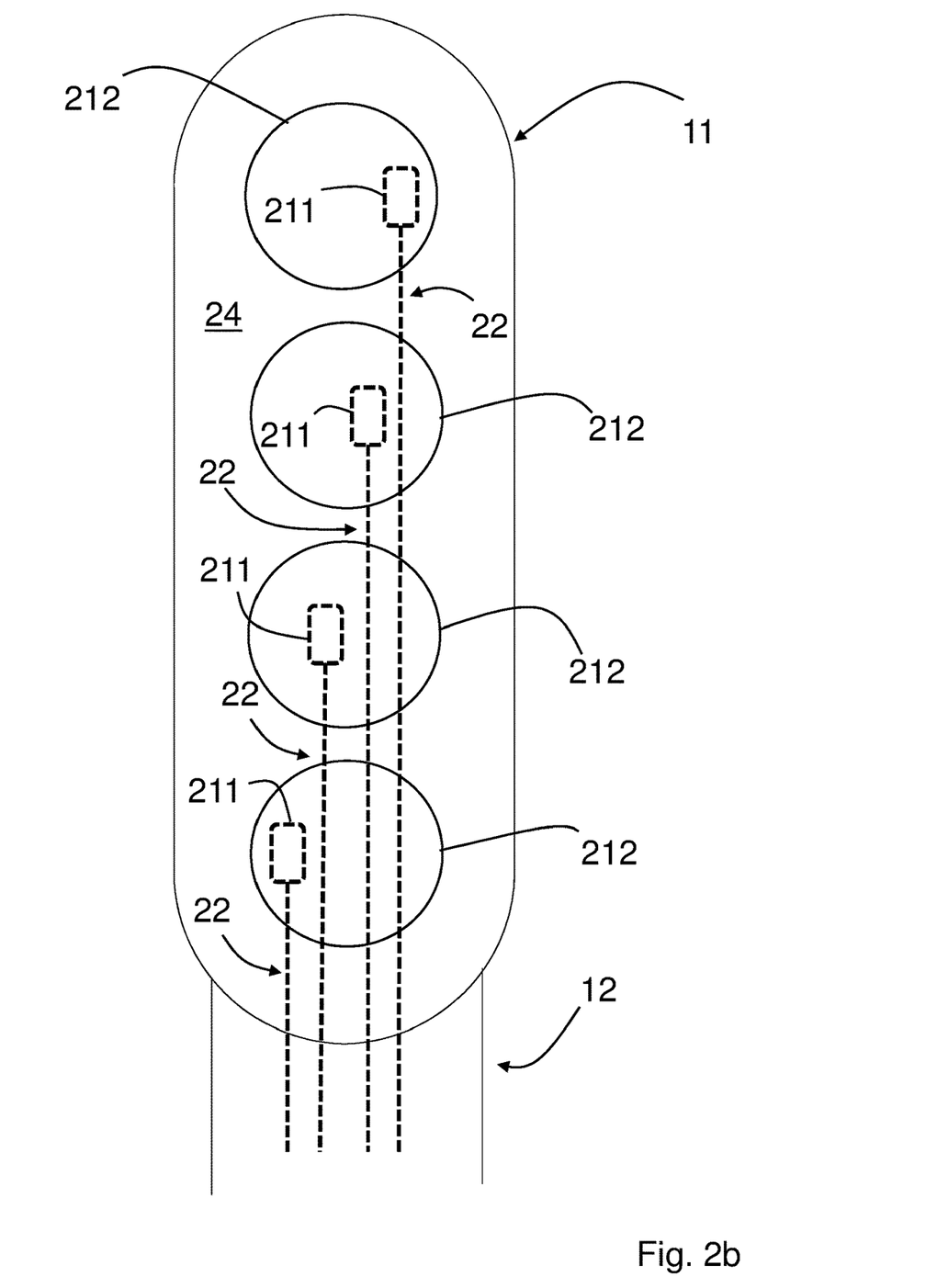
FIG. 2b is a detail of the head end of the electrode of the present invention according to one embodiment.

FIG. 2b shows a detail of the head end 11 of the electrode of the present invention according to a preferred embodiment.

Particularly such embodiment provides the use of the second layer of metal material.

According to such configuration, each head contact is composed of a first layer of conductive ink, particularly a conductive ink plate 211 and a second layer of metal material, such as for example a conductive contact element 212 overlapping the plate 211.

The head end 11 therefore is composed of a layer of flexible material, a layer of conductive ink being deposited thereon.

The deposition of conductive ink allows conductive tracks 22 and plates 211 to be formed, as well as tail ends 23 to be formed, not shown in the figure.

After depositing the conductive ink, a layer of insulating material 24 is deposited which preferably covers and insulates the conductive tracks 22, leaving the plates 211 free from it.

Then a second layer of metal material is deposited, in the form of conductive contact elements 212.

The conductive contact elements will be placed in contact with the patient brain and will allow EEG signals to be recorded.

Each conductive contact element 212 overlaps a corresponding plate 211, with which it is in contact.

As it is clear from figures, the conductive contact elements 211 have a recording area greater than plates 211: this allows EEG signals to be best recorded which anyway will be transmitted to the plate 211, by means of the overlapping interface between conductive contact elements 212 and plates 211.

The provision of the insulating material layer 24 allows conductive tracks 22 to be insulated from conductive contact elements 212, allowing the latter to use most of the available surface to obtain particularly large recording areas with respect to the reduced dimensions of the head end 11, required by the specific application of the electrode of the present invention.

It is clear how such configuration can be used to obtain various head contact shapes, still while maximizing the recording area with respect to the dimension of the head contact.

The electrode obviously can provide any number of conductive tracks 22, as well as of head contacts 21 and tail contacts 23, on the basis of operating needs.

In addition to the number of head contacts 21 and tail contacts 23 it is possible to provide different shapes of the head ends 11 and tail ends 13, as well as it is possible to provide different shapes of the intermediate part 12.

Based on the use, generally the intermediate part 12 and the tail end 13 have shapes completely similar to those shown in FIGS. 1 and 2.

However it is particularly important from a functional perspective, the possibility of modifying the shape of the head end 11: FIGS. 4a to 4f show some of the possible embodiments for such head end 11 of the electrode of the present invention.

The possibility of providing any shape and any number of contacts is guaranteed by the lack of constructional constraints, obtained by the method for making the electrode.

FIGS. 3a to 3d schematically show the steps of such method.

Figure 3A:
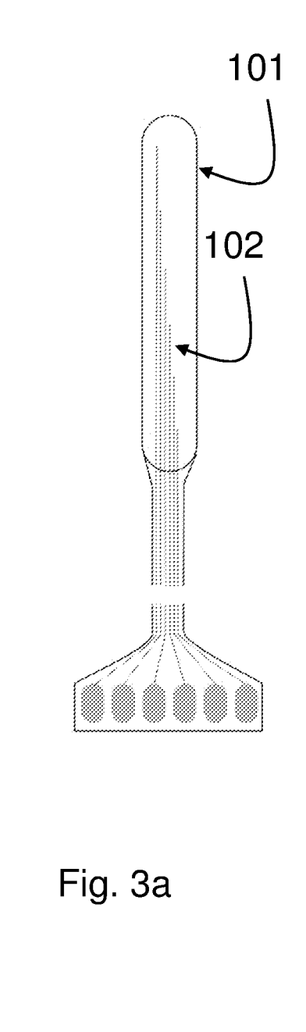
FIGS. 3a to 3d are steps of the method for making the electrode of the present invention.

Starting from a layer of flexible material 101, such as for example a sheet of biocompatible material, conductive ink 102 is provided to be deposited on said sheet, FIG. 3a, such to form one or more conductive tracks.

In the variant shown in FIG. 3a, the conductive ink 102 is deposited to form both conductive tracks 22 and tail contacts 23, but it is possible to form conductive tracks 22 and tail contacts 23 is different moments, as well as it is possible to provide the conductive ink to be deposited in a single moment to form conductive tracks 22, tail contacts 23 and head contacts 21.

Figure 3B:
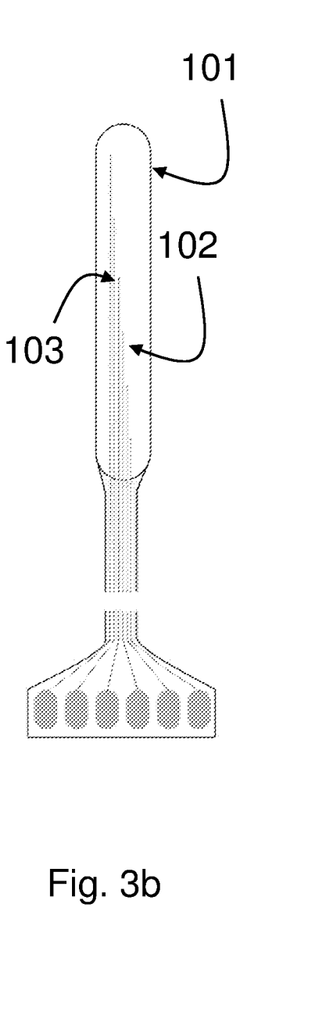

After depositing conductive ink 102 a layer of insulating material 103 is provided to be deposited such to form one or more insulating tracks interposed between conductive tracks, such as shown in FIG. 3b.

Preferably the layer of insulating material completely covers the electrodes, expect for head contacts 21 and tail contacts 23.

Figure 3C:
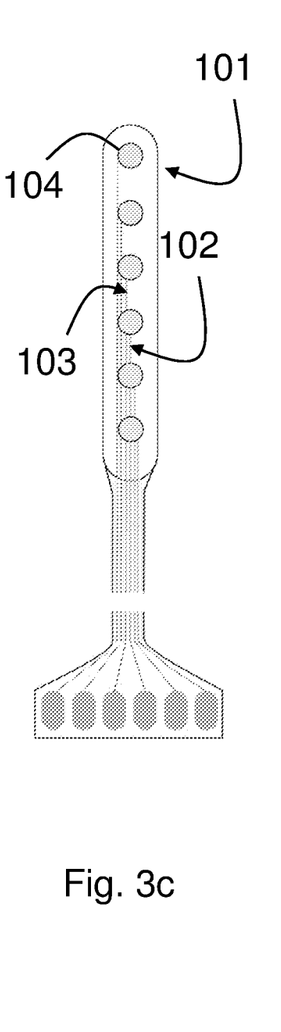

FIG. 3c shows head contacts being formed, by depositing a first layer of conductive ink 104 at the head end of the electrode.

As said above such step can be provided at the same time with the step described for FIG. 3a.

Figure 3D:
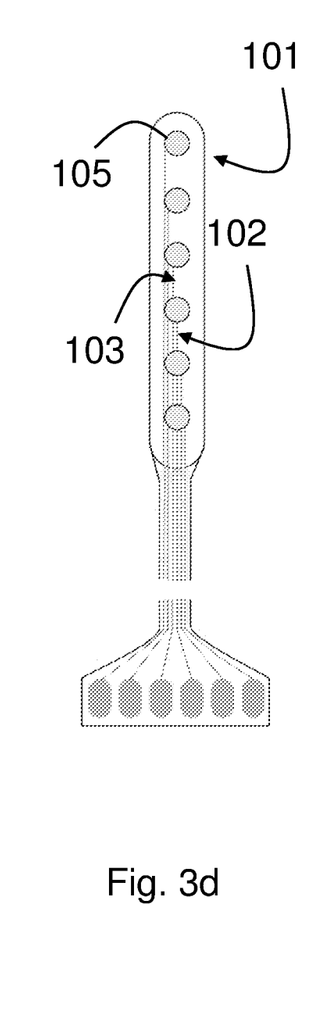
Figure 4A:
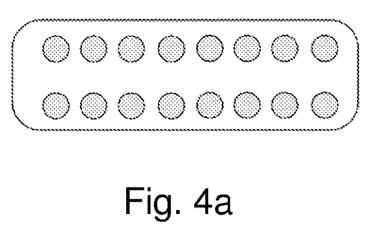
FIGS. 4a to 4f are some possible arrangements of the head end of the electrode of the present invention.
Figure 4B:
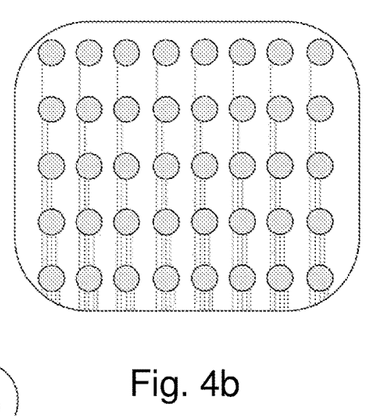
Figure 4C:
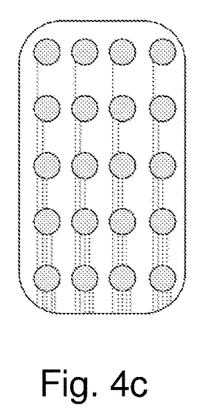
Figure 4D:
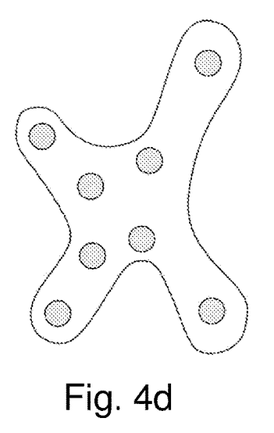
Figure 4E:
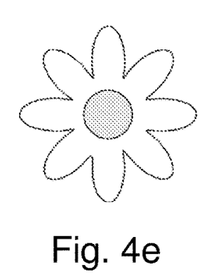
Figure 4F:
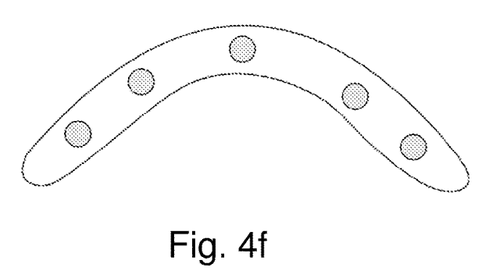

Then, FIG. 3d, a second layer of metal material 105 is deposited, at the head contact.

Advantageously the step just described of depositing the second layer of metal material takes place by galvanic coating.

Finally it has to be noted that in the figures showing the method of the present invention, the layer of flexible material 101 is shown already cut with the final shape of the electrode.

However it is possible to start from a rectangular sheet, to carry out all the deposition steps, and then to cut the several electrodes in the desired shapes.

As an alternative it is possible to start from a rectangular sheet, to deposit the conductive ink to form the tail contacts, head contacts and conductive tracks, to cut the electrodes and then to subject them to galvanic coating.

Figure 5A:
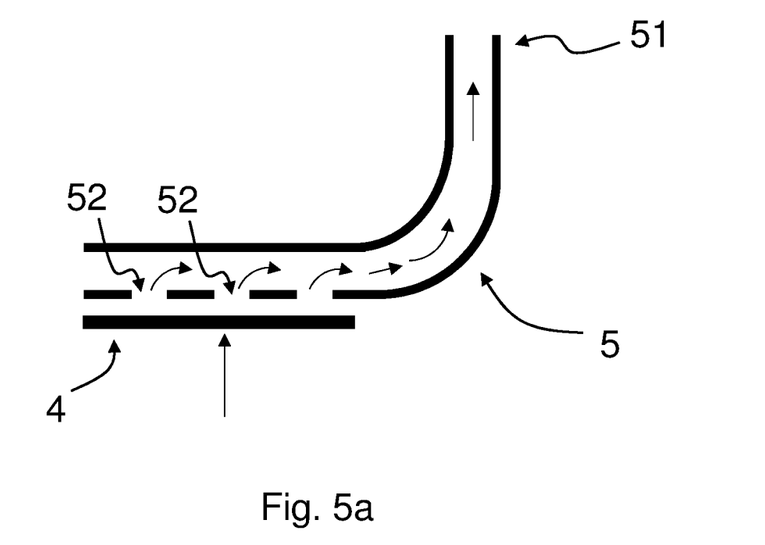
FIGS. 5a and 5b are a diagram of a possible embodiment of the kit of the present invention.
Figure 5B:
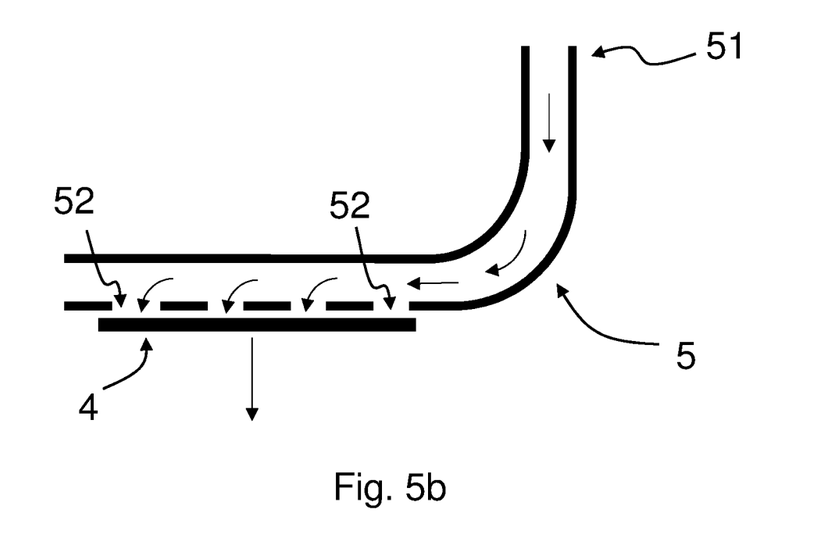

FIGS. 5a and 5b schematically show a possible embodiment of the kit of the present invention.

The kit comprises an electrode 4 and a support element to allow the electrode 4 to be inserted into the patient skull, where a hole is perforated.

The electrode 4 preferably is made according to one or more of the characteristics described above.

The support element on the contrary is composed of a cannula 5, two longitudinal sections thereof being shown in FIGS. 5a and 5b.

The cannula 5 has at least one end 52 allowing the cannula 5 to be connected to any suction system, for example a syringe.

The cannula 5 is composed of a tubular element having holes 52 perforated on side walls of the cannula 5, in any number and with any size.

Such as shown in figures, the electrode 4 is placed on the side walls of the cannula 5 to cover the holes 52.

FIG. 5a shows the suction step: after placing the electrode 4 air is drawn (arrows denote the motion direction of air) such that the electrode is perfectly adherent to walls of the cannula 5: the electrode 4 approaches the cannula 5 in the direction denoted by the arrow.

Thus the cannula 5 maintains the electrode 4 in place, the cannula 5 is inserted in the patient skull and then, FIG. 5b, air is fed into the cannula (arrows show the motion direction of air) to release the electrode, in the direction denoted by the arrow, at the region of the brain where the stimulation and/or recording have to take place, while maintaining the electrode 4 adherent to the brain.

The invention claimed is:

1. A cortical stimulating and recording electrode comprising:
   a flexible support element having a head end and a tail end;
   a head contact, a tail contact, and a conductive track arranged on the flexible support element, the head contact and the tail contact being respectively arranged at the head end and tail end and being connected by the conductive track, such that said conductive track transmits signals from said head contact to said tail contact and vice versa,
   wherein said conductive track is formed of a layer of conductive ink deposited on said flexible support element;
   a layer of insulating material overlapping at least the conductive track but not the head contact and the tail contact; and
   a conductive contact element overlapping the head contact and a portion of the flexible support element surrounding the head contact, the head contact and the conductive contact element each having a planar shape, a lower surface of the conductive contact element directly contacting an upper surface of the head contact, the conductive contact element being insulated from the conductive track by the layer of insulating material and providing a larger cortical stimulating and recording surface than the upper surface of the head contact.

2. The stimulating and recording electrode according to claim 1, wherein there is provided a plurality of head contacts, tail contacts, and conductive contact elements, each conductive element connecting one of the plurality of head contacts to one of the plurality of tail contacts, the layer of insulating material providing at least an insulating track interposed between neighboring conductive tracks.

3. The stimulating and recording electrode according to claim 1, wherein said head contact and said tail contact each comprise a plate having a first layer of conductive ink.

4. The stimulating and recording electrode according to claim 3, wherein said conductive contact element is produced by binding a plurality of particles of a metal material deposited on said first layer of conductive ink.

5. The stimulating and recording electrode according to claim 1, wherein said head contact comprises a plate comprising a first layer of the conductive ink in contact with the conductive contact element comprising a second layer of metal material.

6. The stimulating and recording electrode according to claim 5, wherein said head end has the flexible support element on which the first layer of the conductive ink is deposited intended to provide at least said plate,
   a third layer of insulating material being provided that covers partially said head end except for at least a part of said plate, and
   the second layer of the metal material being deposited at said plate and completely covering said plate.

7. The stimulating and recording electrode according to claim 1, wherein said flexible support element is configured as a tubular element.

8. A method of making a cortical stimulating and recording electrode, comprising:
   (a) depositing conductive ink on a first layer of flexible material to form a plurality of head contacts, tail contacts, and conductive tracks connecting head contact to each tail contact;
   (b) depositing a second layer of insulating material overlapping the conductive tracks but not the head contacts and the tail contacts; and
   (c) depositing a third layer of a metal material to form conductive contact elements disposed to overlap the head contacts and portions of the first layer surrounding the head contacts,
   wherein the head contacts and the conductive contact elements each have a planar shape, a lower surface of each of the conductive contact elements directly contacting an upper surfaces of a corresponding head contact.

9. The method according to claim 8, wherein the conductive ink forming the head contacts and/or the tail contacts is deposited after forming said conductive tracks.

10. The method according to claim 8, wherein depositing the third layer of the metal material comprised depositing the third layer with a galvanic coating.

11. The method according to claim 8, wherein depositing the third layer of the metal material comprises binding a plurality of particles of the metal material.

\* \* \* \* \*